(12) United States Patent
Ashmead et al.

(10) Patent No.: US 9,597,458 B2
(45) Date of Patent: **\*Mar. 21, 2017**

(54) FLUOROPOLYMER BARRIER MATERIALS FOR CONTAINERS

(75) Inventors: Edgar G. Ashmead, Lincoln University, PA (US); Edward C. Gunzel, Oxford, PA (US); Michael P. Moritz, Media, PA (US)

(73) Assignee: W. L. Gore & Associates, Inc., Newark, DE (US)

( \* ) Notice: Subject to any disclaimer, the term of this patent is extended or adjusted under 35 U.S.C. 154(b) by 0 days.

This patent is subject to a terminal disclaimer.

(21) Appl. No.: 13/117,573

(22) Filed: May 27, 2011

(65) Prior Publication Data

US 2012/0251748 A1 Oct. 4, 2012

Related U.S. Application Data

(63) Continuation-in-part of application No. 12/915,850, filed on Oct. 29, 2010, now Pat. No. 8,722,178.

(60) Provisional application No. 61/256,156, filed on Oct. 29, 2009.

(51) Int. Cl.
| | |
|---|---|
| *B32B 27/32* | (2006.01) |
| *B32B 7/02* | (2006.01) |
| *A61M 5/315* | (2006.01) |
| *B32B 1/00* | (2006.01) |

(Continued)

(52) U.S. Cl.
CPC ....... *A61M 5/31513* (2013.01); *A61M 5/3202* (2013.01); *A61M 2005/3118* (2013.01); *A61M 2005/3131* (2013.01); *A61M 2207/00* (2013.01); *Y10T 156/1043* (2015.01); *Y10T 428/1321* (2015.01); *Y10T 428/1352* (2015.01); *Y10T 428/1359* (2015.01); *Y10T 428/1376* (2015.01); *Y10T 428/24992* (2015.01); *Y10T 428/3154* (2015.04)

(58) Field of Classification Search
None
See application file for complete search history.

(56) References Cited

U.S. PATENT DOCUMENTS

| | | | | |
|---|---|---|---|---|
| 4,964,866 | A | \* 10/1990 | Szwarc | 604/192 |
| 5,009,646 | A | \* 4/1991 | Sudo et al. | 604/230 |
| 5,112,664 | A | 5/1992 | Waterland, III | |

(Continued)

FOREIGN PATENT DOCUMENTS

| | | |
|---|---|---|
| EP | 0 375 778 | 7/1990 |
| EP | 1 317 937 | 6/2003 |

(Continued)

OTHER PUBLICATIONS

Wattpad, Thermoplastic Elastomers, WP Technology, retrieved Jul. 15, 2013, p. 1.\*
International Search Report PCT/US2010/054750, 13 pages.

*Primary Examiner* — Callie Shosho
*Assistant Examiner* — Patrick English
(74) *Attorney, Agent, or Firm* — Amy L. Miller

(57) ABSTRACT

A container having a barrier layer is provided. The container may be of thermoplastic and the barrier may inhibit materials from leaching from the thermoplastic material or from extraction of compounds from medicants by the thermoplastic. A process is also described that allows for molding thin barrier layers as container lines and for forming thermoplastic containers with barrier liners.

8 Claims, 10 Drawing Sheets

(51) Int. Cl.
　　　*A61M 5/31*　　(2006.01)
　　　*A61M 5/32*　　(2006.01)

(56) References Cited

U.S. PATENT DOCUMENTS

| | | |
|---|---|---|
| 5,279,606 A | 1/1994 | Haber et al. |
| 5,879,789 A * | 3/1999 | Dolan et al. .................. 428/212 |
| 6,030,694 A | 2/2000 | Dolan et al. |
| 6,090,081 A | 7/2000 | Sudo et al. |
| 6,331,351 B1 | 12/2001 | Waters et al. |
| 6,541,589 B1 | 4/2003 | Baillie |
| 6,960,195 B2 | 11/2005 | Heinz et al. |
| 7,111,848 B2 | 9/2006 | Tachikawa et al. |
| 7,521,010 B2 | 4/2009 | Kennedy et al. |
| 2003/0004491 A1 * | 1/2003 | Tenhuisen et al. ........... 604/502 |
| 2009/0093602 A1 | 4/2009 | Ford |
| 2012/0251748 A1 | 10/2012 | Ashmead et al. |
| 2012/0260607 A1 | 10/2012 | Moritz |

FOREIGN PATENT DOCUMENTS

| | | |
|---|---|---|
| EP | 2374497 | 10/2011 |
| GB | 0399336 | 10/1993 |
| JP | S6485665 | 3/1989 |
| JP | 2004305307 | 9/1989 |
| JP | H01138454 | 9/1989 |
| JP | H09507802 | 8/1997 |
| JP | 200286481 | 3/2002 |
| JP | 2006288652 | 10/2006 |
| WO | WO 99/17816 | 4/1990 |
| WO | WO 94/13469 | 6/1994 |
| WO | WO01-60534 | 8/2001 |
| WO | WO 03/095552 | 11/2003 |
| WO | WO 2009/082034 | 7/2009 |
| WO | WO 2011/059823 | 5/2011 |

* cited by examiner

FLUOROPOLYMER BARRIER MATERIALS FOR CONTAINERS

RELATED APPLICATIONS

The present application is a continuation-in-part application based on U.S. patent application Ser. No. 12/915,850, filed Oct. 29, 2010, now U.S. Pat. No. 8,722,178 which claims the benefit of Provisional No. 61/256,156, filed Oct. 29, 2009, the subject matter of which is specifically incorporated herein by reference.

BACKGROUND OF THE INVENTION

Syringes used for delivery of medicaments are principally constructed of a barrel and a stopper. The stopper is slidably fitted within the syringe barrel and may have a stopper rod affixed to it for actuation of the syringe and delivery of medicament. The stopper is generally constructed of an elastomer, with silicone oil applied. The silicone oil is applied to reduce sliding friction between the stopper and barrel and to improve the seal between them. The oil allows for ease of sliding when administering a dose which may ensure the full dose can be administered. Partial dosing is of particular concern in the case of pens and so-called auto injecting syringes. In such applications, the oil is also critical to prevent jamming of the device which can lead to trauma at the site of injection. The improved sealing provided by silicone oil also may ensure that no foreign contaminants like bacteria enter the syringe.

Recently there has developed a trend favoring pre-filled syringes which function to both store and deliver medicaments. Such pre-filled syringes may offer cost savings to the pharmaceutical industry and may improve safety, convenience and efficacy of medicament delivery. Biopharmaceuticals are an important class of pharmaceuticals that may increase the use of pre-filled syringes and related devices (pens, auto injectors and the like). Such biopharmaceuticals may include insulin, vaccines, antibodies, blood products, hormones, cytokines, and the like. As more pharmaceuticals and particularly biopharmaceuticals utilize delivery in pre-filled syringe and similar devices, the challenges of conventional syringe technology become apparent.

Several aspects of traditional syringe construction present a challenge for their use as pre-filled syringes. The use of silicone oil is a concern, because the oil may degrade the medicament and because a small amount of silicone may be injected with it. The oil may also be of particular concern with regard to biopharmaceuticals because it may cause aggregation of certain proteins.

Another issue that arises in prefilled syringes is that the elastomer of the stopper may contain leachable and extractable contaminants. These may also contaminate the medicament upon long term storage in syringes. Trace amounts of residual monomer or plasticizer or other impurities from the stopper can adversely effect the therapeutic or can have an adverse impact on the patient once injected.

Among the many other considerations affecting prefilled syringe devices and similar devices and their components are the need to be sterilized, stability with transport and storage for up to a few years, optical clarity, the need to integrate into existing filling equipment (including the durability requirements for stopper cleaning and insertion into the syringe barrel), leachables and extractables of all components of the syringe, and the need to maintain sterility from filling through administering of the contents, and finally user preferences and ergonomic considerations. For a variety of reasons the prefilled syringe market uses both glass and plastic barrels.

The foregoing considerations apply in similar manner to other containers, particularly containers suitable for medicaments. For example, rigid tip caps and other container closures as well as syringe barrels may benefit from barrier materials. In some such applications, the improved barrier material may serve as a barrier between the product contained in the container and the environment.

DESCRIPTION OF THE INVENTION

The present invention provides a syringe stopper that is suitable for use in syringes without silicone oil or other liquid lubricants. In one aspect, the invention provides a low friction barrier between an elastomeric stopper material and a therapeutic in the syringe. The barrier may inhibit materials from leaching from the elastomer material or from extraction of compounds from medicants by the elastomer. A process is also described that allows for molding thin barrier layers while allowing adequate bonding with the elastomer.

In another aspect, the inventive barrier material may also be used on non-elastomeric materials such as plastics (polypropylene, polycarbonate, polyethylene, etc) thermoplastics, specifically fluoroplastic materials such EFEP, PVDF, PFA etc.

In certain embodiments, the invention may use barrier films including expanded fluoropolymer films and, particularly expanded polytetrafluoroethylene films. Barrier films based on expanded PTFE can provide for thin and strong barrier layers to leachables and extractables. The superior strength of the expanded fluoropolymer structure allows these materials to form thin barriers which remain intact during the forming process and installation of the stopper into the syringe body.

The use of at least partially porous and advantageously fibrilizing materials, such as ePTFE in combination with barrier materials may provide many advantages. In one aspect, the use of such partially porous materials may provide a scaffold that enables thin strong barrier layers to be made and improves the bond between the elastomer and the barrier. Barrier compliance is critical to maintaining a seal between the stopper and the barrel; porous materials may also provide for improved compliance of the stopper. Improved compliance may result from reduced film thickness, flexural compliance, or the compressibility of one or more layers of the porous material. Accordingly, by providing a barrier that is at least partially porous to the outside of the syringe stopper, the seal between the stopper and syringe barrel may be improved while the sliding force is minimized.

The barriers may be of single layer or multiple layer construction. As described herein, layers may be described functionally. However, the functional names of the various layers in the descriptions of embodiments that follow may not describe all of the potential functions of any given layer. Accordingly, it will be understood that such functional nomenclature is not intended to be limiting of any layer property. For example, a barrier layer may have additional properties and functions such as providing a low friction surface, increasing bond strength and the like. Moreover, in multi-layer embodiments, each layer may contribute to the reduction of leachable and extractable materials regardless of its designation as a barrier layer or otherwise.

Figure 5:
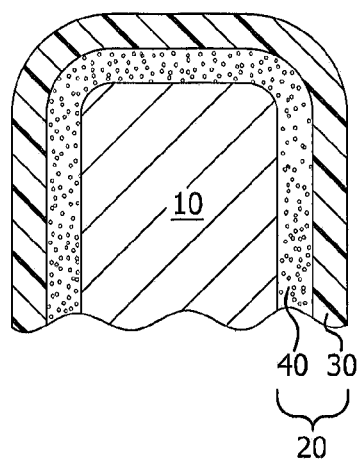
FIG. 5 represents a cross sectional view of a syringe stopper according to one embodiment of the invention.

FIG. 5 shows a first embodiment of syringe stopper of the current invention comprised of an elastomer body 10, and a fluoropolymer barrier 20. The elastomer body 10 can be comprised of any elastomer suitable for the application, most notably rubbers constructed butyl, bromobutyl, chlorobutyl, silicone, nitrile, styrene butadiene, polychloroprene, ethylene propylene diene, fluorelastomers, or blends of any of the foregoing. The materials of the barrier 20 are chosen to provide low coefficient of friction, compliance, low extractables and leachables, good barrier properties as they relate to extractables and leachables from the elastomer body.

Figure 8:
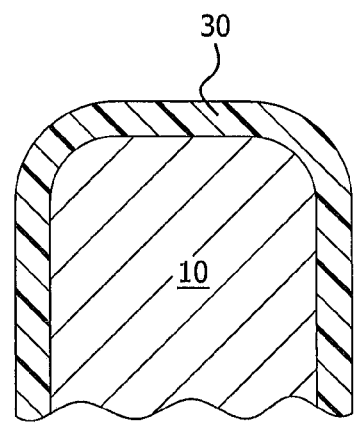
FIG. 8 represents a cross-sectional view of an embodiment of the inventive plunger stopper.
Figure 9:
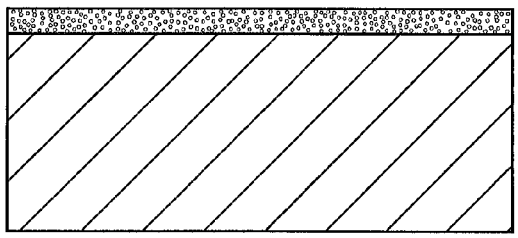
FIG. 9 represents a cross-sectional view of an embodiment of the inventive plunger stopper.

In an embodiment, the barrier (20) may comprise a single layer of densified ePTFE. FIG. 8 shows a syringe stopper of the current invention comprised of an elastomer body, 10, and a barrier layer, 30. The elastomer body may comprise any of these previously mentioned materials. In this aspect, the barrier film may comprise densified expanded fluoropolymer, preferably densified ePTFE.

A densified ePTFE film may be obtained in the manner described in U.S. Pat. No. 7,521,010 to Kennedy, et al. The densified expanded PTFE film is then combined with an elastomer to construct a syringe stopper. In this embodiment, the densified ePTFE film is thermoformed to make a preform. Thermoforming is done at process temperatures sufficiently above the nodal melt to ensure melt forming while preserving barrier and strength properties. The high strength expanded film allows for forming extremely thin barrier films. Barrier films can be made with thicknesses ranging from 0.5 micron to 20 microns. The films are preferentially less than 30 microns. The film can optionally be pre treated or post treated with chemical etching, plasma treating, corona, roughening or the like to improve bonding to the elastomer body.

The thermoformed, densified ePTFE preform can be combined with the elastomer body by injection molding, compression molding, priming and post laminating around an elastomer perform, or other suitable means. Examples of elastomers that can be used to form the elastomer body include silicone, butyl, nitrile, polyurethane, fluoroelastomers, styrene ethylene butadiene styrene elastomers, styrene butadiene rubbers, and the like.

In another embodiment, the barrier 20 may comprise a composite fluoropolymer film having a barrier layer 30 and a porous layer 40. The barrier layer 30 can be comprised of densified ePTFE, PTFE, fluorinated ethylene propylene (FEP), polyethylene, polypropylene, polyvinylidene fluoride, polyvinylfluoride, perfluoropropylevinylether, perfluoroalkoxy polymers, and the like. The porous layer 40 can be comprised of ePTFE or other porous expanded and advantageously fibralizing fluoropolymers (for example, ePTFE as taught in U.S. Pat. No. 6,541,589). The ePTFE layers may advantageously be filled with an organic or inorganic material to provide color lubricity or other function.

In another embodiment a barrier is constructed by coating or otherwise depositing a barrier polymer onto the porous expanded layer to create a composite film. One such example of this would be to deposit granular or powdered fluoropolymers such as powdered PTFE onto the porous ePTFE surface in a coating process. The ePTFE support should be constructed to be thermally stable enough to allow heat treatment of the deposited fluoropolymer for the creation of a barrier or for bonding of the deposited layer to the porous ePTFE support.

Figure 6:
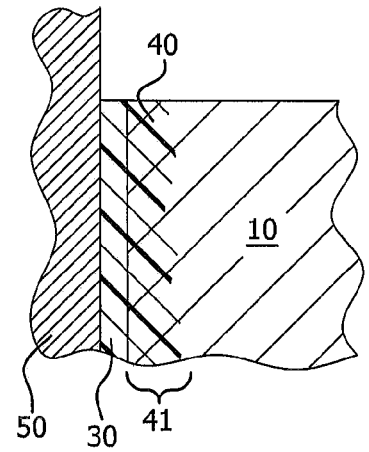
FIG. 6 represents a cross sectional view of a syringe stopper according to another embodiment of the invention.

In certain embodiments, elastomer material may advantageously penetrate the porous structure of the barrier. FIG. 6 shows a cross-section of a stopper according to an embodiment depicting the syringe barrel wall, 50, the barrier film, 30, the porous layer, 40, and the elastomer body, 10. Specifically, this figure shows a region of partial penetration 41 of the elastomer material into the porous structure, 40. Penetration of the elastomer material into the porous structure may improve the bond between elastomer and barrier.

Figure 7:
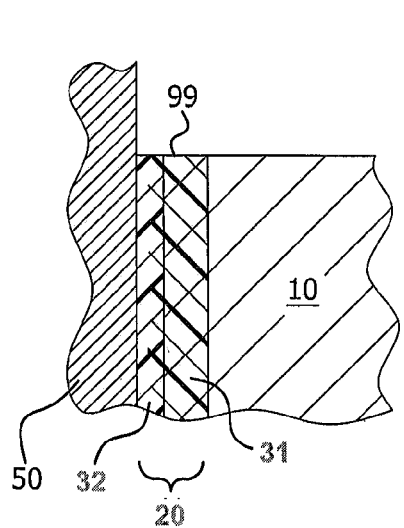
FIG. 7 represents a cross sectional view of a syringe stopper according to another embodiment of the invention.

FIG. 7 shows a cross-section of another embodiment of a syringe stopper according to the invention including the syringe barrel wall 50, a barrier 20, and an elastomer body 10. The barrier is comprised of a barrier layer 32, and a porous layer 31. In this embodiment, the barrier layer 32 comprises a coating deposited onto the porous layer 31. The barrier layer may comprise a polymer at least partially imbibed into the porous layer 31 in a manner that creates a porous layer composite section 99. This porous layer composite section 99 may improve bonding of the barrier polymer to the porous layer. The porous composite section 99 may also provide support for the barrier polymer to impart strength, toughness, compliance and stability which may be beneficial in both the forming process and in the application.

In an aspect, the barrier layer 32 may comprise an imbibed barrier polymer applied in a manner that allows leaves certain sections the porous layer exposed on the surface. In this aspect the porous layer may be sufficiently exposed to allow the exposed sections to come in contact with the syringe wall, 50. In this aspect, the porous polymer is advantageously comprised of ePTFE or other suitable lubricious, expanded porous fluoropolymer. The exposed sections of fluoropolymer may reduce the coefficient of friction of the barrier film against the wall.

Figure 10A:
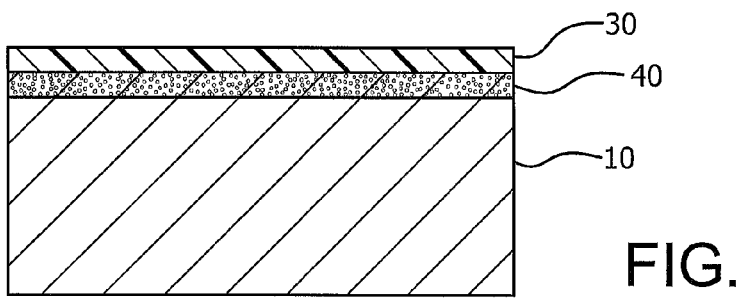
FIG. 10 represents a cross-sectional view of an embodiment of the inventive plunger stopper.
Figure 10B:
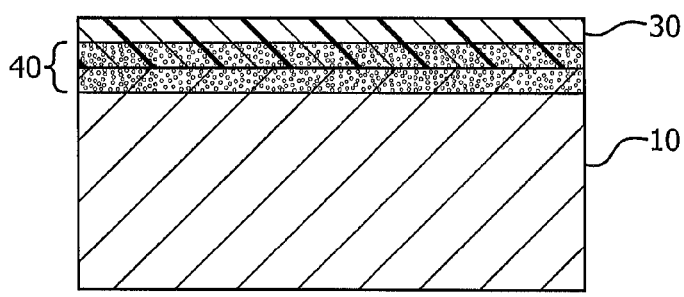

In many of the embodiments of the invention, a porous layer is disposed between the barrier layer surface and the elastomer of the stopper. The inventive stopper may advantageously include various degrees of penetration of either elastomer material or barrier polymer into the porous material as shown in FIGS. 9 through 13. FIG. 10A is a cross-sectional view of the stopper showing the elastomer layer (10) and a composite layer comprising a fluoropolymeric barrier layer (30) and a porous ePTFE layer (40). In the embodiment depicted in FIG. 10B, the elastomeric material from layer (10) substantially fills the pores of the ePTFE layer (40).

Figure 11:
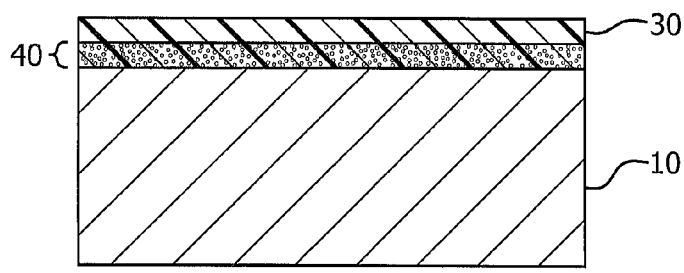
FIG. 11 represents a cross-sectional view of an embodiment of the inventive plunger stopper.
Figure 12:
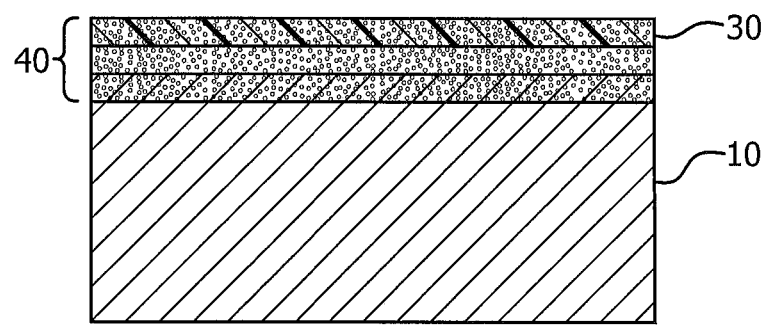
FIG. 12 represents a cross-sectional view of an embodiment of the inventive plunger stopper.
Figure 13:
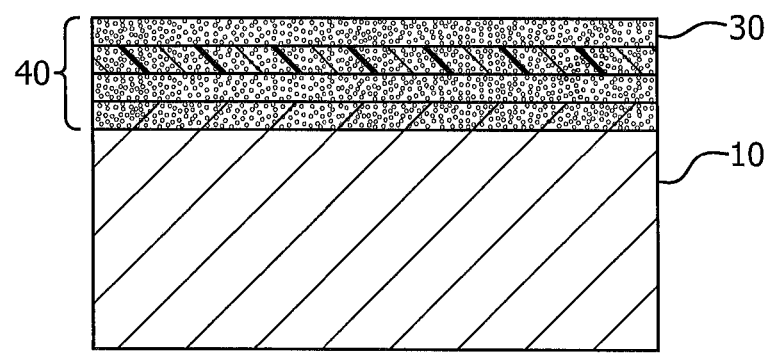
FIG. 13 represents a cross-sectional view of an embodiment of the inventive plunger stopper.

Alternatively, the barrier polymer (30) may substantially fill the porous structure (40), as shown in FIG. 11. In another aspect, the porous material (40) is filled to a substantially similar degree with barrier polymer (30) and elastomer (10), leaving few open pores in the porous structure as in FIG. 10B. In still another aspect, both the barrier polymer and the elastomer partially fill the porous structure, while leaving some open pores between them as shown in FIG. 12. Other variations of penetration of elastomer and or barrier fluoropolymer may be readily apparent, one such variant shown in FIG. 13. Each may have advantages according to the specific application, with due consideration to the various desirable characteristics of the finished device, such as reduced friction, improved barrier properties, and improved sealing. The degree of penetration of either barrier polymer or elastomer may be controlled by any means known, but include variations in time, temperature, pressure, and porosity of the porous material. In one aspect the porous material may, for example have a porosity that varies with depth.

In still another embodiment, the barrier may comprise a composite of a densified ePTFE film and a thin layer of porous ePTFE bonded to the barrier layer film. A densified ePTFE film may be obtained as described in U.S. Pat. No. 7,521,010 to Kennedy et al. The ePTFE/densified ePTFE composite may be combined in the manner described in U.S. Pat. No. 6,030,694 to Dolan, et al.

In this embodiment, a composite barrier comprises a layer of densified ePTFE film and a porous ePTFE layer. The porous ePTFE layer is constructed in a manner that it retains most of its porosity through thermoforming. It is also sufficiently compliant that it improves sealability against the syringe barrel wall. To accomplish this, at least a portion of the porous layer may remain sufficiently open after thermoforming and post compression molding with the elastomer. This open porosity allows some compressibility which may aid in the conformability and seal of the stopper to the surface.

The thickness of the densified ePTFE film would be suitably tailored to the application with pre-thermoform thicknesses of less than 100 microns, more preferably, less than 50 microns, more preferably less than 30 microns. Additionally, the flexural rigidity of the composite film would need to be suitably tailored to ensure compliance and sealability while retaining sufficient strength for this application.

The ePTFE porous layer would be preferably less than 150 microns thick. To improve performance as a bonding layer, the ePTFE porous layer should be made sufficiently open to allow for at least partial penetration of the elastomer into the porous (i.e. and fibrillated structure onto the surface of the nodes or fibrils) during elastomer forming.

To construct the barrier preform, the composite barrier may be thermoformed at temperatures, rates and pressures suitable to allow the densified film to form to the shape of the female cavity of a stopper mold. The more porous ePTFE layer may be oriented toward the inside of the mold cavity, while the densified ePTFE barrier layer will be oriented toward the outer wall of the mold. The thermoforming can be done at temperature ranges suitable to form the ePTFE based film, without fracturing or otherwise disturbing the barrier provided by the densified ePTFE barrier layer. Suitable temperatures could be in the range of 330-400° C., more preferably 350-380° C. at pressures suitable to form without fracturing the barrier layer, or substantially collapsing the porous layer.

The thermoformed barrier preform may be integrated with an elastomeric syringe stopper of the current invention by, for example, by injection molding or compression molding an elastomer like butyl rubber or silicone or Viton®. The porous ePTFE layer can be advantageously made stable to the elastomer injection or compression molding process, thereby maintaining some of its porous structure. The porous structure may improve the bond of the elastomer to the barrier. This may result in improved compliance for sealability, as the porous layer allows for some compressibility for better, low force sealing.

In yet another embodiment, a barrier can be made by forming a thin densified composite comprising a porous ePTFE layer and a thermoplastic barrier layer. In this aspect, a thermoplastic having a surface with a low coefficient of friction is preferred. Accordingly, fluoropolymer based thermoplastics such as FEP, PFA, THV may be applicable. A barrier according to this aspect may be an FEP/ePTFE laminate obtained by following the process taught in WO 94/13469 to Bacino. The barrier may be formed at process temperatures above the softening temperature or even above the melt of the FEP film in a female cavity mold.

The composite barrier of ePTFE and FEP described may allow forming of surprisingly thin, strong barrier films. In this embodiment, the ePTFE layer may act as a support during shape forming to allow thin barrier films. The porous ePTFE layer may also act as a reinforcement to the thermoplastic layer to maintain film strength and integrity of the barrier layer as described above, the ePTFE porous layer can also serve as a bonding layer when a portion of the ePTFE is allowed to remain porous and oriented toward the inside of the mold.

Subsequent combination of a composite film with an elastomer through, for example, compression molding can allow the porous portion of the ePTFE to be adhered to by partial penetration of the elastomer into the porous structure. Alternatively, if the ePTFE/FEP composite barrier is fully imbibed in a manner that leaves no residual porosity in the composite film, the composite barrier film can be chemically modified by etching or plasma or physically modified by roughening, for example, to allow bonding to the elastomer. In another aspect, the ePTFE porous layer can be comprised of multiple layers of ePTFE, each having varying pore size and structure. This multi layer construction may facilitate control of the degree imbibing of the barrier polymer or the elastomer or to allow other desired properties.

One surprising element of some embodiments of the current invention is that the porous film portion of the expanded fluoropolymer layer can maintain its structure through thermoforming and post injection or compression molding of the elastomer. This allows for some of the advantages described above including improved compliance and sealability as well as improved bond between the barrier film and the elastomer body.

In another embodiment, composite barrier is made by laminating a ePTFE porous layer to a densified ePTFE barrier layer using a thin layer of an adhesive, for example, a fluoropolymer thermoplastic like PFA. In this embodiment, a syringe stopper of the current invention can be made by combining composite barrier with an elastomer layer such that the thermoplastic bonds the densified ePTFE barrier layer and the porous ePTFE layer. The ePTFE porous layer of the composite barrier is bonded to the elastomer i.e. stopper material during the molding process.

A composite film could be made by starting with a multilayer porous expanded fluoropolymer film and substantially densifying one or more of the porous layers. In an aspect, the porous layer may be densified by application of pressure during the molding or syringe insertion process.

In another aspect, a porous expanded fluoropolymer film could be formed, then post applied to create a barrier layer. In one embodiment, this could be done by choosing an ePTFE film of suitable deformation characteristics that it allows for deformation into the mold at relatively low temperatures (less than 200° C.). Such a suitable ePTFE film might, for instance, have tensile properties demonstrating high elongation, or low modulus at the deformation temperature. The ePTFE film can be formed into the female mold cavity through a variety of means including through the use of air pressure, through the use of a male mold form, or other suitable means to allow forming of the ePTFE. One method would be to form such an ePTFE film during the injection or compression molding process. This would allow for a structure wherein the ePTFE comprised the outermost layer of the syringe stopper. The pore structure, thickness, and other properties can be suitably tailored to allow controlled penetration of the elastomer into the expanded fluoropolymer layer. In one embodiment, the elastomer is allowed to penetrate through the expanded fluoropolymer film, allowing for a composite structure of expanded fluoropolymer film and elastomer at the outer surface. If the outer surface is suitably dense and nodal, it can allow for significantly reduce friction relative to the elastomer itself. A preferred embodiment utilizes a stopper created using the aforementioned process of forming an ePTFE film in a female mold, then post laminating, imbibing or coating a barrier onto the ePTFE's outermost surface. In the coating and imbibing processes, the ePTFE can be used to control the barrier thickness.

A syringe stopper of the current embodiment could be comprised of a composite barrier comprised of multiple porous layers or multiple barrier layers or both. The properties of a composite barrier so constructed can be more suitably tailored to allow optimal compliance through the properties of the thin films while providing low surface friction against the barrel and adequate barrier properties to leachables, extractables and gas permeation.

Another means of making the ePTFE syringe stopper with porous outer and creating a barrier layer would be to post densify the ePTFE with pressure and temperature.

It will be appreciated that there are many variations of the processes described herein could be utilized without departing from the invention. Some of these variations may include, but are not limited to, the following:

Any of the ePTFE fluoropolymers used in syringe stopper of the current invention could be made with an expanded fluoropolymer film based on PTFE, modified PTFE, and PTFE and TFE copolymers such as, for example, the resins as described in U.S. Pat. No. 6,541,589 and US Patent publication 2009/0093602.

There are also a wide variety of processes for forming the film and attaching it to the elastomer body which may be utilized without departing from the invention. In addition to what is described above, one could form an ePTFE film at low temperatures.

In another aspect, the invention provides an improved tip cap for a syringe. A tip cap may be provided as a protective covering to a syringe needle. Accordingly, a tip cap may provide a seal to the end of the needle to prevent contamination of a medicament. As with a syringe stopper, a tip cap construction that minimizes leachable and extractable components is desirable. Moreover, the tip cap must be readily removable. Moderate friction between the tip cap and needle is preferred. The tip cap according to the present invention therefore may be of construction similar to that of the syringe stopper. In contrast to the stopper, however, the barrier layer is positioned in the tip cap to be adjacent to the needle on final assembly. As the challenges between tip cap and stopper are similar, each of the constructions described herein with regard to stoppers may be adapted for use in a tip cap construction.

In another aspect, the invention provides an internal barrier layer for a container. The container may be of a material without barrier properties. The addition of a barrier layer to the inside surface of the container may improve barrier properties of the container. The container may be made of any material, including thermoset material, thermoplastic material, metal, ceramic or glass.

The container may be of a variety of materials. Advantageously, the container is selected from materials that will form a bond with the barrier layer. In one aspect, the container is advantageously formed from thermoplastic material. The container constructed of thermoplastic may be formed separately or simultaneously with the barrier layer. Preferably, the barrier layer is pre formed to a shape approximating the inside of the container. The container and the preform may be placed together into a mold and formed under appropriate heat and pressure to the final shape of the container with barrier layer. In this aspect the barrier layer may form a strong bond with the thermoplastic of the container during the final molding process.

In another aspect, the container may be a thermoset plastic. Thermoset plastics may be injected into the mold at the time of final molding of the barrier or barrier composite perform. In another aspect, the thermoset plastic may be formed or made by other means separately from the perform. In this aspect, the container of the thermoset plastic may function as the mold, and the barrier layer or composite barrier layer maybe molded to the thermoset material.

The barrier may be selected from a number of combinations described herein. In one aspect, the barrier is a composite of a densified expanded fluoropolymer, such as ePTFE. The densified, expanded fluoropolymer may include copolymers of ePTFE. The densified expanded fluoropolymer may be combined with a thermoplastic such as FEP or EFEP to form a barrier composite.

During the molding process, additional layers may be added to the barrier layer or composite barrier layer to construct a container or to improve bonding of barrier or barrier composite to the container. For example thermoplastic layers may be added to improve bonding to a thermoplastic container. In one embodiment PVDF sheet may be added to the molding process. The PVDF layer may add some rigidity to a thermoplastic container. In some embodiments, a relatively thick thermoplastic film may be formed in the mold to make the container. In another embodiment, a porous ePTFE film may be added between the thermoplastic layers to improve bonding between them.

The barriers and composite barriers of the present invention have shapes that are uniquely high aspect. Various measures are known in the art which reflect the aspect of the molded part. Included among these are several common expressions of draw ratio, including areal draw ratio, linear draw ratio, and height to diameter ratio.

Each of these measures is understood to reflect the work put into a thermoplastic during the molding process of simple shapes. From such measures the relative difficulty of maintaining barrier integrity in the molding process can be inferred. While such measures are useful, they do have limits in their ability to characterize complex shapes and to completely account for the thinning and breakdown of the barrier properties of when molding such shapes.

In order to better account for complex molded shapes, the shape factor may be used. As used herein, the shape factor is a ratio of the major diameter of the edge of a barrier to the maximum length of a cross section perimeter of the barrier. The edge of the barrier is defined as the intersection of an interior surface of the barrier and an exterior surface of the barrier. For example, for a syringe stopper, the barrier may be of generally convex shape. The interior surface of the barrier is oriented towards the glass syringe barrel and the exterior surface oriented towards the elastomeric material of the stopper. The barrier edge is the circular region at the intersection of the interior and exterior surface. The major diameter of the exemplary syringe is therefore the diameter of a circle defined by the barrier at the end of the stopper. The major diameter may also be understood to account for irregularly shaped barriers. The major diameter is considered the diameter the largest circle generally in plane with the barrier edge that would contact some point on the edge. The maximum cross section length is the longest length of the barrier perimeter in a cross section of the barrier made perpendicular to the major diameter.

In some constructions the shape factor may be conveniently determined with regard to measurements of the mold itself. In simple cylindrical shaped male and female molds for example, the major diameter may be approximated by the mold diameter, and the maximum cross section perimeter length be calculated from the mold dimensions.

Figure 18A:
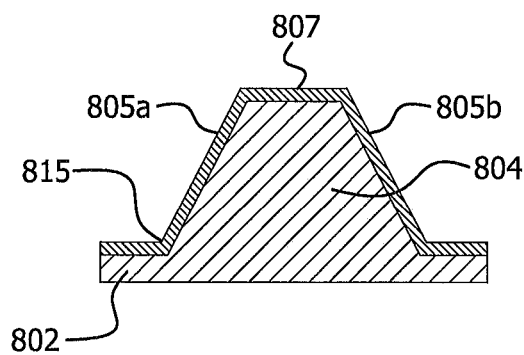
FIGS. 18a and 18b illustrate a cross sectional view and top view respectively, of a vial stopper having a barrier layer.
Figure 18B:
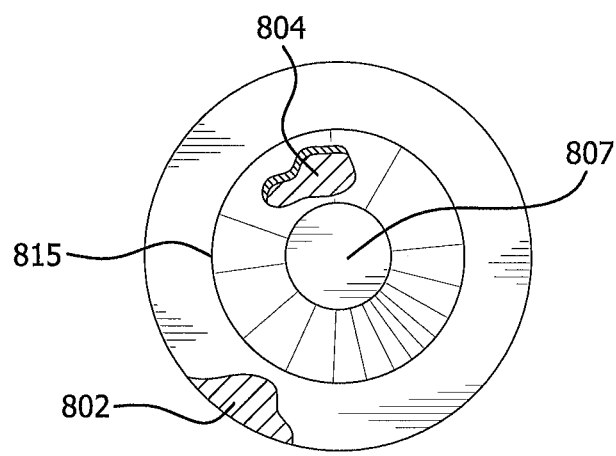

In other embodiments, the molded barrier may be of more complex shape. For example, a molded barrier may have a generally low aspect when the entire barrier is considered, but include features which are of high shape factor within the barrier or mold. In such embodiments, the maximum shape factor is best calculated with reference to the specific features having shape factors. In such cases, the major diameter may be considered to be the major diameter of the feature and the cross section length determined with reference to the feature and not the entirety of the molded barrier. For example, with reference to FIGS. 18A and 18B, the molded barrier 801 used in connection with a vial stopper 803. The vial stopper has a insertion plug portion 804 and a flange portion 802. In this example, the major diameter of the barrier may be determined with reference to the insertion plug portion of the stopper rather than the larger diameter of the flange portion. The major diameter of the insertion plug portion may be measured at the intersection 815 of the insertion plug portion and the flange portion. Similarly, the maximum cross section length may ignore the flange of the stopper. The maximum cross section is calculated as the sum of the perimeter length of each side 805a and 805b of the plug and the perimeter length of the end of the plug 807. The perimeter length of flange portion 802 is not included in the calculation. In this manner, the forming challenge may be most properly considered by the shape factor. The shape factor for several examples is tabulated below:

TABLE 1

| Sample | Example 9 | Example 2 | Example 10 | Example 11 |
|---|---|---|---|---|
| Major Diameter (mm) | 7.84 | 8.76 | 12.7 | 15.9 |
| Cross Section Length (mm) | 36.49 | 16.56 | 63.5 | 47.7 |
| Shape Factor | 4.7 | 1.9 | 5.0 | 3.0 |

Breaking and Sliding Friction Test

The following procedure was used to evaluate the static and dynamic friction of embodiments of the invention. Each test syringe was attached to a variable pressure pump (Barnant Air Cadet—model 420-3901) by securing a ¼" OD, ⅛" ID silicone tube to its tip (the tip was not fitted with a needle). The stopper assembly with the barrier film was positioned in the syringe to be at the bottom of its motion (closest to the tip). At the beginning of each test, the pressure was slowly adjusted starting at 2 psi and increasing about 1 psi every 30 seconds until syringe stopper movement was initiated (away from tip). The pressure to initiate movement was noted as P break. After the movement was initiated, the pressure was reduced to the lowest level that still allowed sliding. This pressure was noted as P sliding. All pressures were recorded in PSI. The test provided relative data on sliding properties.

Air Leak Test

The same apparatus and setup as described above was then used to evaluate air leakage. The syringe stopper was attached to the pressure pump. However, in this test the stopper was moved to the topmost position within the syringe (farthest from the tip) and the syringe assembly was placed in a 2 Liter glass beaker filled with deionized water. The pressure was set to 3 psi. If no leaks were detected (any sign of visual bubble formation) after 5 minutes, the pressure was increased by 1 psi. This procedure was repeated on each syringe until leaking occurred (or about 15-17 psi when the air was sufficient to eject the syringe stopper from the barrel). The minimum pressure required to cause an observable leak after 5 minutes was recorded in psi. This test was used for evaluating air leakage on Examples 1A, 1B, 1C.

For Examples 1-8 and the comparative example, air leakage was evaluated by performing the test as specified by I.S. EN ISO 7886-1:1998 Annex B, with the following exceptions: i) A bourdon tube gauge was used in place of a manometer, and ii) Deionized water in place of freshly boiled water.

Static and Dynamic Force Test

The test was performed as specified by I.S. EN ISO 7886-1:1998 Annex G, with the following exceptions: i) Syringe is mounted so that nozzle is pointing down, ii) No liquid was expelled; only air was expelled, and iii) Forces resulting form travel from the total graduated capacity position to 20 mm from that point were recorded.

Static force is defined as the value at the first inflection point in the force versus displacement graph. Dynamic force is the value after 15 mm of travel.

Toluene Exposure Test

Figure 14:
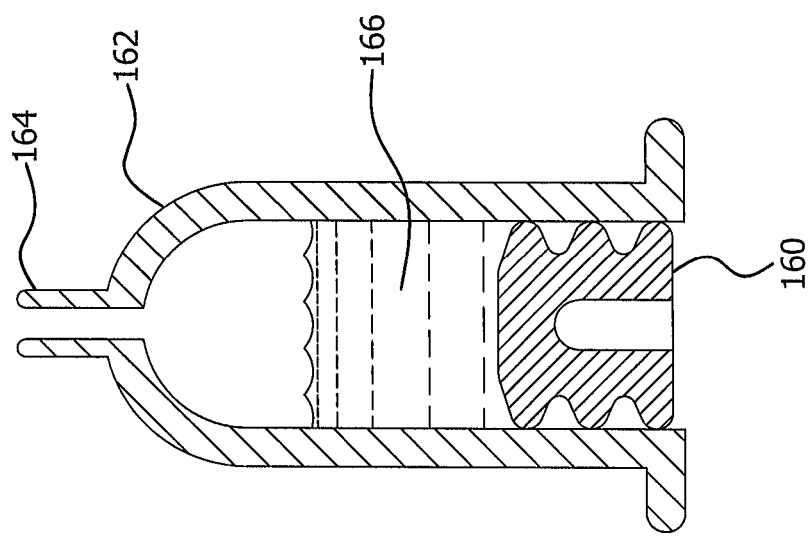
FIG. 14 is a schematic illustration of the test apparatus for accessing the barrier properties of a stopper.
Figure 16:
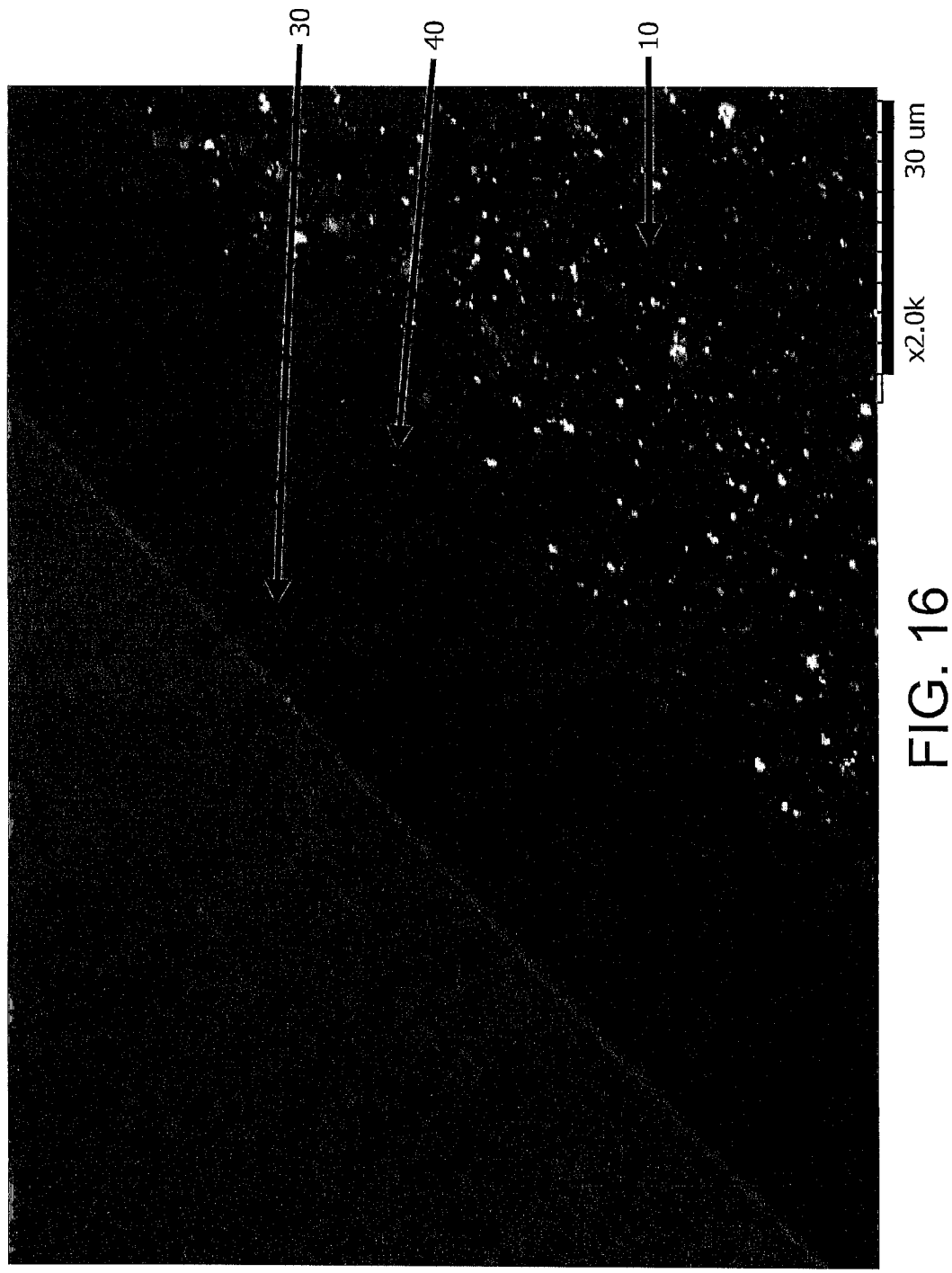
FIG. 16 is an SEM image showing a cross-section of an embodiment of the invention.

This test was used to assess the barrier properties of stoppers. A schematic illustration of the test apparatus is shown in FIG. 14. The initial weight of the stopper was measured using a balance. The stopper (160) was loaded into the barrel (162) of a glass syringe. 1 ml of Toluene (166) was introduced into the barrel through the luer port (164). The luer port was sealed using a tip cap. The entire apparatus was left under the lab hood for 5 hours at room temperature. After 5 hours, the Toluene was removed from the barrel using a syringe. The stopper was removed from the barrel using compressed air. Upon removal of the stopper, it was quickly dried using a Kimwipe® and immediately weighed using the balance. Lower the weight gain of the stopper compared to its initial weight, the more effective its function as a barrier. Less than 1 mg weight gain of the stopper may indicate an effective barrier.

Vent Tube Installation Procedure

Figure 15:
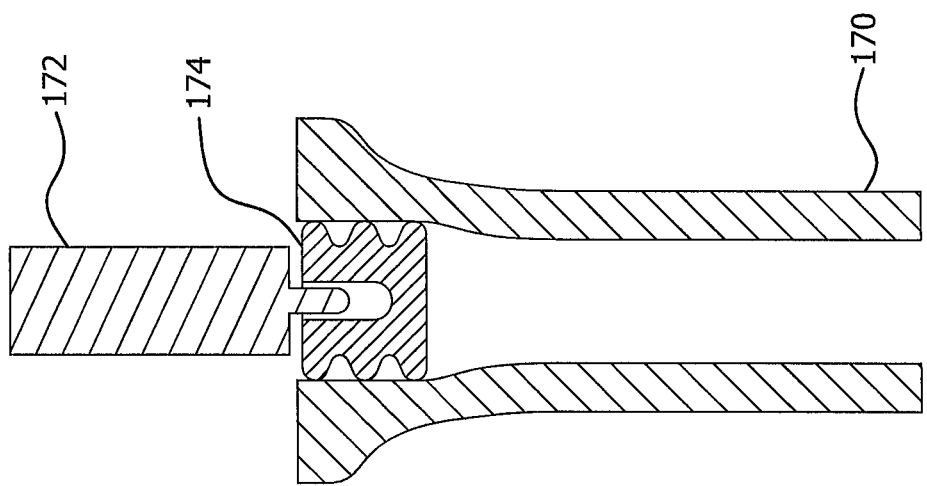
FIG. 15 is a schematic illustration of a test apparatus to determine the durability of a stopper to the vent tube installation test.

FIG. 15 describes a schematic of the test apparatus comprising a vent tube (170) meant for a 1 mL standard stopper (as specified in ISO11040-5) and a plunger (172). The vent tube, part of a SVH200 Semiautomatic Stoppering Machine from Groninger was used in this procedure. The apparatus was loaded into a universal testing machine capable of moving the plunger at a rate of 0.7 meters/sec. As shown in FIG. 15, the stopper (174) was placed on to the top of the vent tube (170). The test was initiated by moving the plunger at a rate of 0.7 meters/sec to push the stopper through the vent tube. The test was complete when the stopper traversed the entire length of the vent tube.

Tensile, Modulus, Strain to break

Materials were evaluated for tensile strength, modulus and strain to break according to ATM D882-10 using 0.25 inch by 3 inch samples and a cross head rate of 20 inches/min and one inch gauge length.

EXAMPLES

Example 1A, 1B and 1C

Examples of certain embodiments of the invention were constructed using a single layer of densified ePTFE films as the barrier. The films were obtained by process described in U.S. Pat. No. 7,521,010 to Kennedy, et al. The films had thicknesses of 25 microns, 10 microns, and 5 microns, respectively. Eight commonly available disposable plastic syringe barrels and stoppers with shafts were obtained. Four were 1 ml plastic syringes and four were 3 ml plastic syringes. Each included an elastomer stopper comprising a butyl rubber. The syringes were thoroughly washed with 95% hexane to remove any silicone oil. The washed syringe barrels and stoppers were allowed to dry for 5 days on an airhood to ensure complete evaporation of the hexane. Syringe stoppers were made by taking a densified ePTFE film and applying it to the stopper. Samples were made using these different film thicknesses. The films were first heated by a heat gun (Karl Leister, CH 6056—Hotwind S) set at 600° C. at a distance of about 6-8 inches from the nozzle. The films were then drawn around the stopper in the presence of the heat (thereby using the stopper as a male plug or mold). Care was taken to ensure that the film was adequately heated so that it would readily form without distorting the stopper shape and the heat of the heat gun did not deform the stopper. The four densified ePTFE wrapped stoppers were installed into the silicone free plastic syringe barrels for subsequent testing.

The table below demonstrates the performance as measured by the breaking and sliding friction test and the air leak test of each wrapped stopper compared to a silicone oil control. It can be seen that the thin densified ePTFE films showed better performance than the relatively thicker films with respect to providing an airtight seal. This was in part due to unavoidable wrinkling around the stopper contours in this process.

TABLE 2

| Syringe Type | Film Cover | P break, (psi) | P slide, (psi) | P, min air leak (psi) |
|---|---|---|---|---|
| (1 mL) | Example 1A 1 mil Densified EPTFE | 14 psi | 12 psi | 1 psi |
|  | Example 1B 0.4 mil Densified EPTFE | 14 psi | 13 psi | 10 psi |
|  | Example 1C 0.2 mil Densified EPTFE | 9 psi | 8 psi | 13-15 psi |
|  | None/Silicone Oil | 7 psi | 6 psi | 16-18 psi |
| BD (3 mL) | Example 1A 1 mil Densified EPTFE | 8 psi | 6 psi | 1 psi |
|  | Example 1B 0.4 mil Densified EPTFE | 5-6 psi | 3 psi | 1 psi |
|  | Example 1C 0.2 mil Densified EPTFE | 5 psi | 3-4 psi | 7 psi |
|  | None/Silicone Oil | 4-5 psi | 2-3 psi | >20 psi |

Other embodiments of the present invention were constructed using a process of thermoforming a barrier preform and molding an elastomer material within the form to construct a syringe stopper.

Example 2

Figure 1:
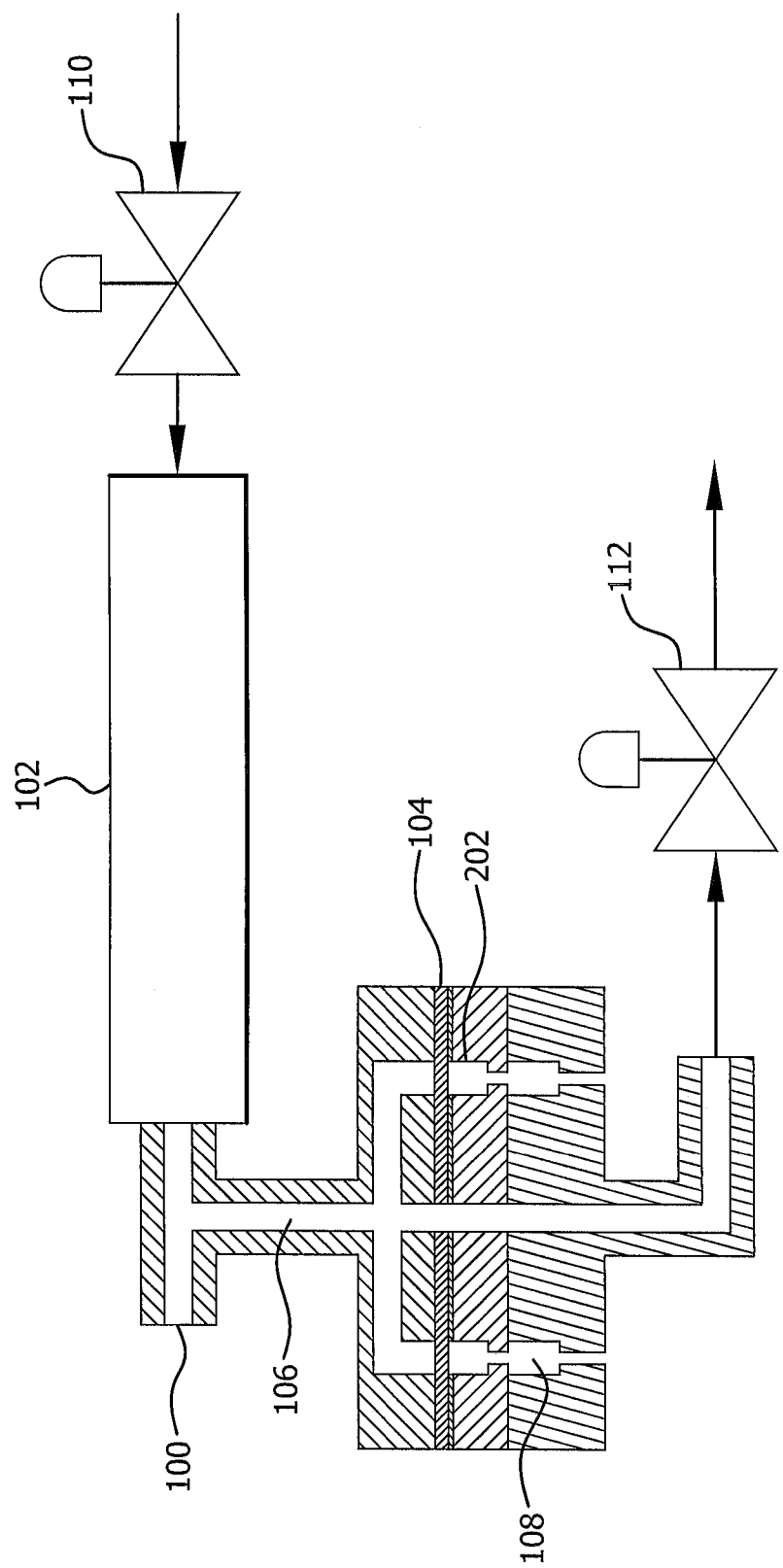
FIG. 1 is a schematic representation image of the thermoforming equipment used to make most of the barrier film preforms.
Figure 2:
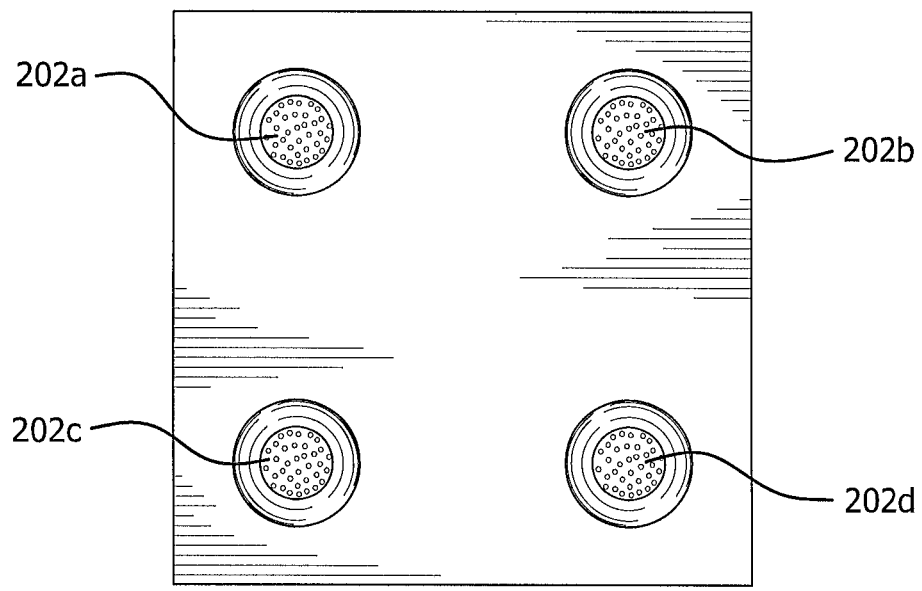
FIG. 2 depicts the 4-cavity mold that was used in the above mentioned thermoforming equipment.
Figure 2:
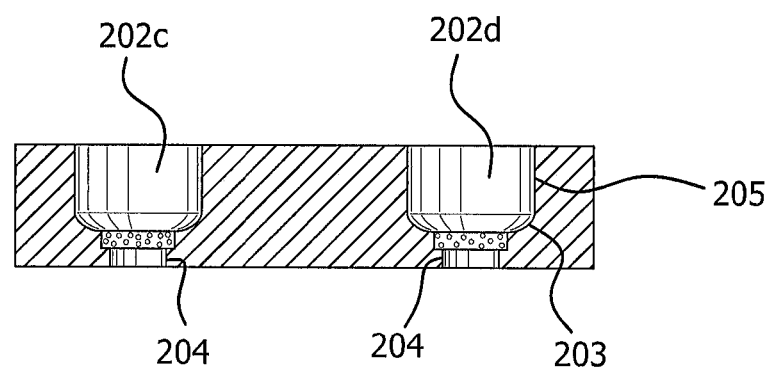

A barrier was created from a single densified ePTFE film 1.7-1.8 mil thick, which was obtained by the process described in U.S. Pat. No. 7,521,010 to Kennedy, et al. The film (104) was placed in the thermoforming equipment as depicted in FIG. 1 using the mold depicted in FIG. 2. The thermoforming equipment (100) uses hot air to heat the mold (200), and the pressure drop through the apparatus supplies the force to form the material. The mold has round cavities (202 a-d) having different dimensions. One of 0.380 inches, one of 0.372 inches, one of 0.365 inches, and one of 0.358 inches. The bottom portion of the cavities have a rounded corner (203) with a radius of 0.079 inches, a side straight wall 205 of 0.188 inch height, and contain a 0.201 inch wide, 2 micron porous stainless steel disc (204) at its bottom most point.

At room temperature a pressure of 5 psi was applied. The heater on the hot air system (102) (Osram Sylvania 6000 W, 240V, 25 A) was activated using a setpoint of 385° C. as measured by the thermocouple (106) above the mold. Once a temperature of 360° C. was reached below the mold cavities, as measured by the bottom thermocouple (108), the system was held for 5 minutes. Pressure was then increased by increasing the inlet air flow using the hot air system inlet valve (110). The pressure was increased at a rate of approximately 3 psi/minute from 5 psi to 13 psi. Above 13 psi, the pressure was increased at approximately 1 psi/minute up to 18 psi. This pressure was sufficient to form the densified ePTFE sheet. The sample was held at this pressure for 5 minutes, and then the heater was deactivated allowing the mold and film to cool. The mold was allowed to cool to below 50° C., as measured by the bottom thermocouple, before removing the sample. Any technique suitable for heating both the material and the mold as well as adding the air pressure to form the material will suffice. For example the mold may be simply bolted together and placed in an oven or heated press with an air line to supply the pressure. Other processes known for thermoforming, bladder forming or vacuum forming may also be used.

Figure 3:
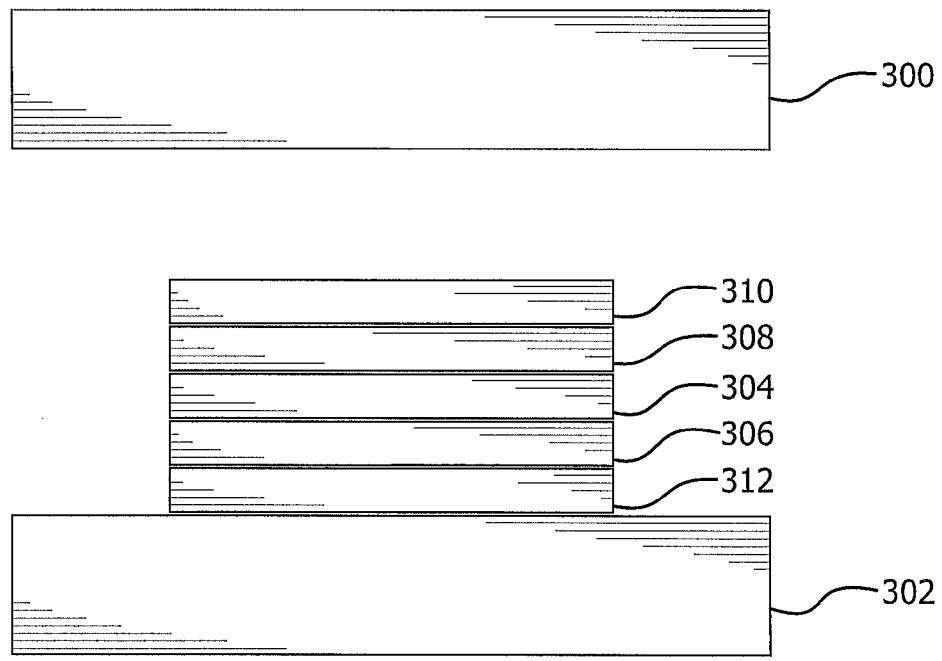
FIG. 3 is a representative drawing of the lay-up in the press for compression molding.

To coat the inside of the barrier with an elastomer solution, sample cavities were filled with a 10% by weight solution of the elastomer in MEK and allowed enough time to dry so that a substantial amount of the solvent was evaporated. Each cavity was loaded with 1-1.5 grams of elastomer (Viton GF-600S from DuPont compounded with varox D8PH and Diak 7 and processed to a crumb (304) by Eagle Elastomer Inc., Cuyahoga Falls, Ohio). The mold (306) along with the above thermoformed densified ePTFE sheet was loaded into a press with both platens (300, 302) preheated to 100° C. As represented in FIG. 3, a 10 mil Aluminum sheet (312) was placed on the lower platen (302). A Kapton sheet (308) and a steel caul plate (310) were placed below the upper press platen (300) to provide uniform pressure. The sample was heated under no pressure for 45 minutes, and then compressed under a force of 8000 lbs. The platens were slowly closed and temperature based set points were used in the following press cycle:

Step 1: Close platens
Step 2: Heat for 10 minutes at 100° C.
Step 3: 5 minutes at 120° C.
Step 4: 15 minutes at 175° C.
Step 5: 1 minute at 30° C.
Step 6: Open platens Samples were then cut from the release sheet using a razor blade, affixed to a stopper rod using an acrylic adhesive (3M Scotch-Weld Structural Adhesive DP-8005) and installed within a standard 1 cc glass syringe barrel free of silicone oil, and tested.

Example 3

A sample was prepared in a manner similar to Example 2 except that the densified ePTFE barrier was formed to shape using a faster pressure ramp rate. The procedure of Example 2 was followed except that a pressure ramp rate of approximately 3 psi/minute from 5 psi to 18 psi was chosen. This ramp rate was obtained by closing only the exit air valve (112). This molding procedure resulted in a barrier film with milky appearance, which may indicate that there was some porosity induced in the material by the speed of the forming process.

The mold cavity was then filled with elastomer, molded and attached to a syringe stopper according to the process described in Example 2. After insertion into a glass syringe barrel the sample was tested.

Example 4

A sample was prepared in a manner similar to that described in Example 2, except that one surface of the densified ePTFE barrier material was textured before it was thermoformed. One side of the densified ePTFE material was deformed using a coarse glass bead sandblaster. The sandblaster nozzle was set to 15 psi and held approximately 9 inches away from the sample, which was affixed to a cardboard backer. The sandblaster was passed 5 times over the entire surface of the sample. This process resulted in significant mechanical deformation on one side of the film which increased the apparent surface roughness.

The barrier material was placed in the mold with the roughened side up so that it would be oriented towards the elastomer. The mold cavity was then filled with elastomer, molded and attached to a syringe stopper according to the process described in Example 2. After insertion into a glass syringe barrel, the sample was tested.

Example 5

A sample was prepared similar to Example 1 except that the densified ePTFE barrier material exposed to a plasma treatment after thermoforming. The material was left in the mold and placed in a plasma vacuum chamber with a 90/10 mix of He/$H_2$ and an exposure time of 10 minutes. This sample was not coated with an elastomer solution before compression molding. Otherwise the procedures of Example 2 were followed.

The mold cavity was then filled with elastomer, molded and attached to a syringe stopper.

Example 6

A sample was prepared in a manner similar to Example 2, except that an ePTFE/PFA composite film was used as a barrier. The barrier was obtained in a manner similar to that described in Example 2 of WO 94/13469 to Bacino. The resulting barrier is an ePTFE material with PFA on one of its side surfaces. The barrier material was placed in the mold with the PFA side of the composite facing upwards, such that after thermoforming the PFA would be oriented towards the inside of the mold. The thermoforming process followed that of Example 2 except that the heater setpoint was 295° C. and the mold cavity setpoint was approximately 275° C. Moreover, the pressure ramp rate in the molding process was approximately 11.5 psi/min from 5 to 18 psi. The composite material was held at 18 psi for approximately 15 seconds before cooling. After the sample was removed from the mold it was inverted so that the ePTFE layer was facing inward.

Example 7

A sample was prepared in a manner similar to Example 2 except that the barrier was an ePTFE/densified ePTFE composite. The barrier was prepared according to the methods disclosed in U.S. Pat. No. 6,030,694 to Dolan. The material was oriented in the mold with the ePTFE side of the composite downward, the molded sample was inverted after thermoforming so that the ePTFE layer was facing inward. In this example the mold that was used had the same mold cavities of diameters identical to those of Example 2 ("A"=0.380 inches, "B"=0.372 inches, "C"=0.365 inches, "D"=0.358 inches.) However, each cavity was a straight cylinder of 0.252 inch height and had a stainless steel porous disc making up the bottom of the cavity.

Example 8

Figure 4:
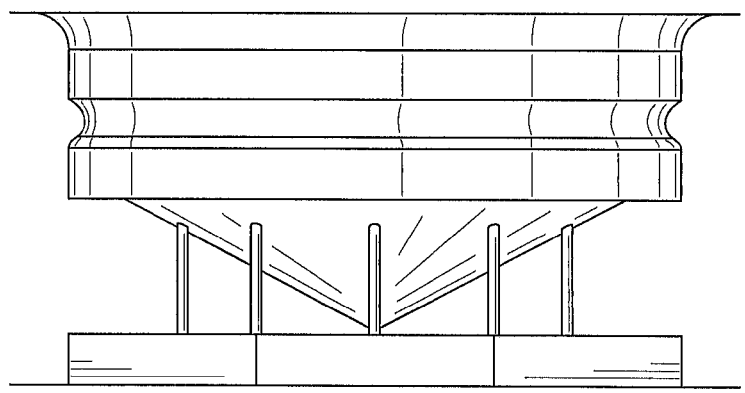
FIG. 4 is a drawing of the cavity used to make the stopper in Example 7.

Another example was constructed using an ePTFE/FEP composite obtained using the procedure described in Bacino. In this example, rather than thermoforming, the film was placed over a mold cavity and formed by compression molding. A single cavity mold was used having a profile depicted in FIG. 4. The mold had a primary diameter of 0.49 inches. The barrier material was obtained using the procedure described in Bacino.

Example 9

A layer of FEP about 0.5 mils in thickness (FEP 100, DuPont) was laminated to a layer of densified expanded PTFE film [Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse)]. The two layers were stacked on top of each other in a pin frame and heating to 380° C. in an oven for 15 minutes. A layer of porous expanded PTFE [thickness: 27.5 micrometers, matrix tensile strength: 66.8 MPa (longitudinal), 75.8 MPa (transverse), strain to break: 131% (longitudinal), 91% (transverse), bubble point: 22.6 psi] was placed on the densified ePTFE-FEP laminate such that the porous expanded PTFE layer faced the FEP layer in the laminate. These three layers were placed between two smooth metal plates, the plates were clamped to a clamping pressure of about 1 psi. The plates were then placed in an oven at 305° C. for 15 minutes. The resulting three layer composite material (densified ePTFE-FEP-porous ePTFE) was then cooled to about 40° C.

This composite material was then thermoformed using heat and vacuum to create a pre-form. The pre-form was constructed by heating the composite to a sufficiently high temperature and then drawing the composite over a male plug using differential pressure. The composite material was loaded into the thermoforming apparatus such that the densified ePTFE layer faced the plug. The composite was heated using a hot air gun (Steinel HG2310) with air exit temperature of 380° C. by placing the gun about 5 mm away from the surface of the composite. After 5 seconds, the film was subjected to a vacuum of −85 kPa. The composite was continued to be heated for another 15 seconds and cooled to about 40° C. under vacuum.

The resulting pre-form sample was then inverted and then placed into a rubber molding cavity charged with 3.5 grams of elastomer (50 Durometer halobutyl rubber), and the stopper was formed by compression molding. The mold was built to geometry specified for 1 mL standard plunger per the ISO standard ISO11040-5:2001(E), with an additional 5% shrinkage factor incorporated.

The cavity was loaded in a press with both platens preheated to 120° C. The platens were closed to 55,500 lbs (about 8700 psi total internal pressure). The platens were then heated at 180° C. for 5 minutes and then cooled under pressure to 40° C. The pressure was released and the stopper was ejected. The resulting stopper was washed using a detergent and triple rinsed with de-ionized water. Stopper samples were then cut from the release sheet using a razor blade. They were subjected to two 30 minute cycles in an autoclave at 121° C. The static and dynamic force on the stopper was measured to be 2.5N and 2.1N respectively. The weight gain of the stopper after the Toluene Exposure test was 0 mg, indicating that the stopper functioned as an effective barrier. Further, the same stopper was subjected to the vent tube placement test and then the Toluene exposure test was repeated. The weight gain was still 0 mg, indicative of superior barrier function of the stopper. The stopper was also tested for leaks using the air leak test and no leak was detected. The areal transformation (%) was calculated to be 82%.

Example 10

A layer of EFEP about 2.7 microns thick (RP-4020, Daikin) was laminated to a layer of densified expanded PTFE film in a manner similar to the one described below. The densified expanded PTFE film had the following properties: Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse). The two layers were stacked on top of each other in a pin frame and heated to 380° C. in an oven for 15 minutes. The resulting two-layer composite barrier (EFEP-densified expanded PTFE) was then cooled to about 40° C.

This composite barrier was then thermoformed using heat and vacuum to create a pre-form. The pre-form was constructed by heating the composite to a sufficiently high temperature to draw the composite over a male plug using differential pressure. The mold consisted of a flat plate with a 60 mm diameter woven fiberglass mat placed over an opening in the center which had a 4.8 mm recess. The male plug was a 12.7 mm diameter pin 25.4 mm in height, and was placed in the center of the mold.

The composite barrier was loaded into the thermoforming apparatus such that the densified ePTFE layer faced the plug. The composite barrier was heated using a hot air gun (Steinel HG2310) with air exit temperature of 380° C. by placing the gun about 5 mm from the surface of the composite barrier. After heating for 5 seconds, the film was subjected to a vacuum of −85 kPa. The composite barrier was heated for another 15 seconds and cooled to about 40° C. while under vacuum.

An aluminum female mold which had a cavity of a geometry to match the thermoforming pin was prepared by heating to 280° C. The mold cavity matched the geometry of the plug with 1.6 mm clearance on all sides. EFEP (RP-4020, from Daikin) resin was provided to the mold. The thermoforming pin, with the pre-form on it, was also heated to 205° C. and inserted into the mold cavity. The entire assembly was cooled to 25° C. After cooling, the molded assembly was removed, providing a container with a wall thickness of approximately 1.6 mm and a PTFE based barrier on the interior of the container. The areal transformation (%) was calculated to be 68%.

Example 11

Figure 17B:
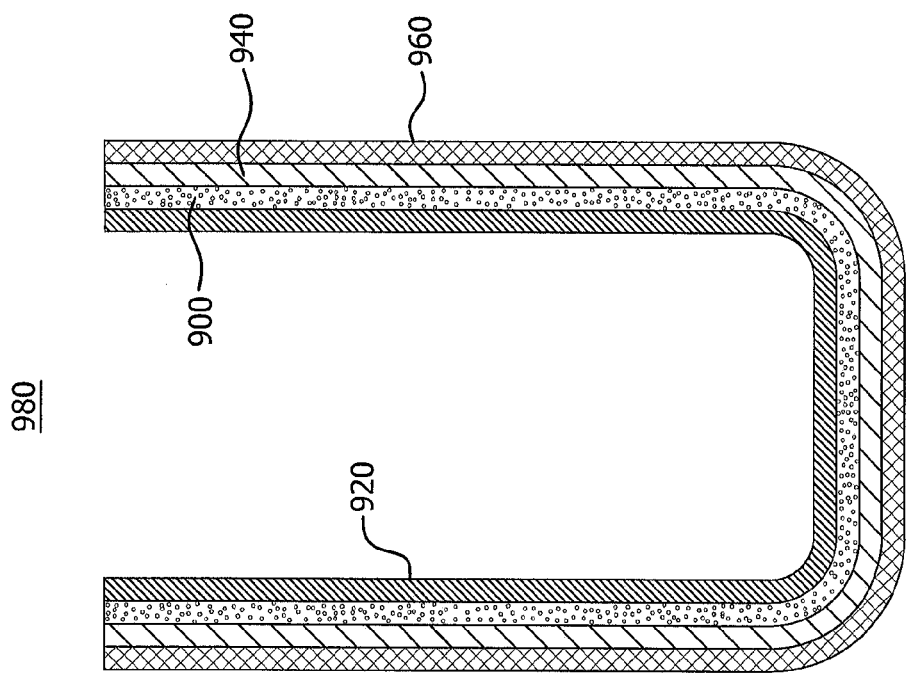
FIGS. 17a and b are schematic illustrations of an embodiment of the inventive container.
Figure 17A:
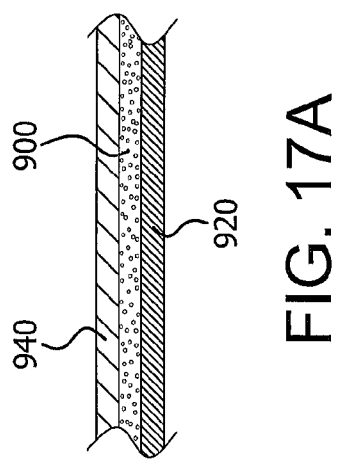

Reference is made to FIGS. 17a and 17b in the following example. A layer of FEP (900) about 0.5 mils in thickness (FEP 100, DuPont) was laminated to a layer of densified expanded PTFE (920) in a manner similar to the one described below. The densified expanded PTFE film had the following properties: Thickness—1 mil; Tensile Strength—13.85 ksi (longitudinal), 13.9 ksi (transverse); Modulus—19.8 ksi (longitudinal), 20.7 ksi (transverse); Strain to Break—425% (longitudinal), 425% (transverse). The two layers were stacked on top of each other in a pin frame and heated to 380° C. in an oven for 15 minutes.

Next, a layer of porous expanded PTFE (940) was placed on the densified ePTFE-FEP laminate such that the porous expanded PTFE layer faced the FEP layer in the laminate. The porous expanded PTFE membrane had the following properties: Thickness—27.5 micrometers; Matrix Tensile Strength—66.8 MPa (longitudinal), 75.8 MPa (transverse); Strain to Break—131% (longitudinal), 91% (transverse); Bubble Point—22.6 psi. These three layers were placed between two smooth metal plates, the plates were clamped to a clamping pressure of about 1 psi. The plates were then placed in an oven at 305° C. for 15 minutes. The resulting three-layer composite material was then cooled to about 40° C.

The three-layer composite material was then thermoformed in combination with an additional layer (960) of 10 mil thick Kynar® 2800 PVDF, hand laid in contact with the porous ePTFE side of the composite. Heat and vacuum were used to create a pre-form. The pre-form was constructed by heating the composite to a sufficiently high temperature to draw the composite over a male plug mold using differential pressure. The three-layer composite material with the additional PVDF layer was loaded into the thermoforming apparatus such that the densified ePTFE (920) layer faced the plug. The mold consisted of a 60 mm sintered stainless steel plate with a 8.3 mm lip on the outer edge and the plug located in the center. The plug was made of stainless steel and had a diameter of 15.9 mm and a height of 15.9 mm.

The composite with the additional PVDF layer was heated using a hot air gun (Steinel HG2310) with air exit temperature of 380° C. by placing the gun about 5 mm away from the surface of the composite. After heating for 5 seconds, the film was subjected to a vacuum of −85 kPa. The composite with the additional PVDF layer was heated for another 15 seconds and cooled to about 40° C. while under vacuum.

The resulting article (980) was shaped in the form of a container and shown in FIG. 17. The areal transformation (%) was calculated to be 118%.

Comparative Example A

Commercial Siliconized Butyl Stopper Made for 1 cc Single Dose Glass Prefilled Syringe

TABLE 3

| Sample | Material | Cavity | Static Force (grams) | Dynamic Force (grams) | Leak pressure (kPa) |
|---|---|---|---|---|---|
| Example 2 | Densified ePTFE | A | 1517.2 | 1232.7 | Pass |
| | | C | 583.5 | 558.1 | Pass |
| | | D | 358.4 | 287.1 | −88 |
| Example 3 | Low porosity ePTFE | A | 1528.4 | 1511.2 | Pass |
| | | B | 915.3 | 880.9 | Pass |
| | | C | 621.8 | 735.6 | Pass |
| | | D | 418.6 | 418.5 | −88 |
| Example 4 | Mechanically deformed densified ePTFE | A | 979.7 | 777.5 | Pass |
| | | B | 734.1 | 612.3 | Pass |
| | | C | 705.5 | 655.5 | Pass |
| | | D | 665.9 | 478.6 | Pass |
| | | B | 1769.2 | 1635.4 | Pass |
| | | C | 844.0 | 638.5 | Pass |
| | | D | 574.6 | 415.3 | −88 |
| Example 6 | ePTFE/PFA composite | A | 2683.8 | 1991.0 | Pass |
| | | B | 2244.4 | 1790.8 | Pass |
| | | C | 1675.3 | 1291.0 | Pass |
| Comparative Example A | Butyl + silicone oil | n/a | 750.5 | 323.7 | Pass |

The invention claimed is:

1. A complex molded article comprising:
   a. an elastomeric body;
   b. a composite layer having a first side consisting of an expanded fluoropolymer and a second side comprising a thermoplastic fluoropolymer; and
   c. a barrier layer comprising a densified expanded fluoropolymer,
   wherein the first side of the composite layer is adjacent to the elastomeric body and the second side of the composite layer is adjacent to said densified expanded fluoropolymer and said densified expanded fluoropolymer is the exterior surface of said molded article, and
   wherein the molded article has a maximum shape factor greater than 3.0.

2. The complex molded article of claim 1 having a maximum shape factor greater than 4.0.

3. A complex molded article comprising:
   a. an elastomeric body; and
   b. a barrier layer comprising:
      a densified expanded fluoropolymer film, and
      a composite layer having a first side consisting of an expanded fluoropolymer and a second side comprising a thermoplastic fluoropolymer,
   wherein the first side of the composite layer is bonded to said elastomeric body and the second side of the composite layer is bonded to the densified expanded fluoropolymer film,
   wherein said densified expanded fluoropolymer film is the exterior surface of said molded article,
   wherein the molded article defines;
      i. an interior space and an exterior space,
      ii. an edge defining the boundary between the interior space and the exterior space, the edge having a major diameter, and
      iii. a cross section perimeter length defined by a cross section of the barrier layer, and
   wherein the ratio of the cross section perimeter to the major diameter is greater than 1.5.

4. The complex molded article of claim 3 wherein the ratio of the cross section perimeter to the major diameter is greater than 3.0.

5. The complex molded article of claim 3, wherein the ratio of the cross section perimeter to the major diameter is greater than 4.0.

6. A complex molded article comprising:
   a. an elastomeric body;
   b. a barrier layer comprising a composite layer having a first side consisting of an expanded fluoropolymer and a second side comprising a thermoplastic fluoropolymer, and
   c. a densified expanded polytetrafluoroethylene (ePTFE) film, wherein the first side of the composite layer is bonded to the elastomeric body and the densified ePTFE film is adjacent to the second side of the composite layer,
      wherein said densified expanded polytetrafluoroethylene film forms the exterior surface of said molded article,
      wherein the molded article has a shape, the shape defining;
         i. an interior space and an exterior space,
         ii. an edge defining the boundary between the interior space and the exterior space, the edge having a major diameter, and
         iii. a cross section perimeter length defined by a cross section of the barrier layer, and
      wherein the ratio of the cross section perimeter to the major diameter is greater than 1.5.

7. The complex molded article of claim 6 wherein the ratio of the cross section perimeter to the major diameter is greater than 4.0.

8. The complex molded article of claim 6 wherein the ratio of the cross section perimeter to the major diameter is greater than 3.0.

* * * * *